United States Patent
Pupek et al.

(10) Patent No.: US 8,969,625 B1
(45) Date of Patent: Mar. 3, 2015

(54) METHOD FOR PRODUCING REDOX SHUTTLES

(75) Inventors: Krzysztof Z. Pupek, Plainfield, IL (US); Trevor L. Dzwiniel, Carol Stream, IL (US); Gregory K. Krumdick, Homer Glen, IL (US)

(73) Assignee: Uchicago Argonne, LLC, Chicago, IL (US)

( * ) Notice: Subject to any disclaimer, the term of this patent is extended or adjusted under 35 U.S.C. 154(b) by 250 days.

(21) Appl. No.: 13/462,012

(22) Filed: May 2, 2012

(51) Int. Cl.
*C07F 9/02* (2006.01)

(52) U.S. Cl.
USPC .......................................................... 568/17

(58) Field of Classification Search
None
See application file for complete search history.

(56) References Cited

U.S. PATENT DOCUMENTS 6,746,794 B2 * 6/2004 Mandal et al. .................. 429/62

OTHER PUBLICATIONS

Lu Zhang, et al., Novel redox shuttle additive for high-voltage cathode materials, Energy Environ. Sci. 2011, 4, pp. 2858-2862.

* cited by examiner

*Primary Examiner* — Clinton Brooks
(74) *Attorney, Agent, or Firm* — Cherskov Flaynik & Gurda, LLC

(57) ABSTRACT

A single step method for producing a redox shuttle having the formula 2,5-di-tert-butyl-1,4-phenylene tetraethyl bis(phosphate) is provided, the method comprising phosphorylating tert butyl hydroquinone with a phosphate-containing reagent. Also provided is method for producing 2,5-di-tert-butyl-1,4-phenylene tetraethyl bis(phosphate), the method comprising solubilizing tert-butyl hydroquinone and tetrabutylammonium bromide with methyltetrahydrofuran to create a mixture; heating the mixture while adding base to the mixture in an amount to turn the mixture orange; and adding diethyl chlorophosphate to the orange mixture in an amount to phosphorylate the hydroquinone.

18 Claims, 2 Drawing Sheets

METHOD FOR PRODUCING REDOX SHUTTLES

CONTRACTUAL ORIGIN OF THE INVENTION

The United States Government has rights in this invention pursuant to Contract No. DE-AC02-06CH11357 between the United States Government and UChicago Argonne, LLC representing Argonne National Laboratory.

BACKGROUND OF THE INVENTION

1. Field of the Invention

This invention relates to a method for producing large amounts of redox shuttle and more specifically, this invention relates to a method for producing at least one kilogram (kg) per batch of a phosphate-containing redox shuttle having a first oxidation potential of approximately 5 volts (V).

2. Background of the Invention

Lithium-ion battery advances are the de facto power sources for portable electronic devices and vehicle propulsion. Rechargeable lithium-ion batteries are used for thousands of cycles with no gaseous exhaust, delivering high density energy and providing reliable and clean chemical energy storage. Compared to fossil fuels and biomass, lithium-ion batteries compare favorably in reducing air pollution and therefore global warming.

As lithium battery chemistry increases in voltage potential, so too does the need to prevent overcharging. One means for preventing overcharging is the use of electronic monitoring devices attached to each cell to monitor voltages.

Another means is the use of anti-overcharge additives to electrolyte. These additives include redox shuttle molecules. Generally, redox shuttle molecules can be reversibly oxidized and reduced at a defined potential slightly higher than the end-of-charge potential of the cathode. This mechanism can protect the cell from overcharge by locking the potential of the cathode at the oxidation potential of the shuttle molecules. Redox shuttles have been implemented for overcharge protection of 3 V class lithium-ion batteries.

Efforts have been made to provide redox shuttles with overcharge protections in excess of 4 volts (V). However, state of the art shuttle production protocols result in extremely small yields (e.g., less than 10 grams). Also, those methods require inert environments and expensive reagents such as chlorodiethyl-phosphite. Reaction 1 depicts a two-step protocol for producing the redox shuttle 2,5-di-tert-butyl-1,4-phenylene tetraethyl bis(phosphate).

Reaction 1:

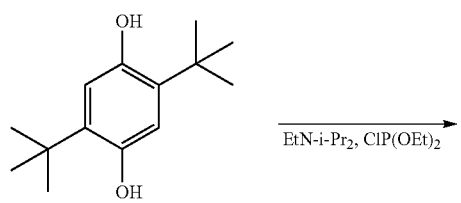

2,5-di-tert-butylbenzene-1,4-diol

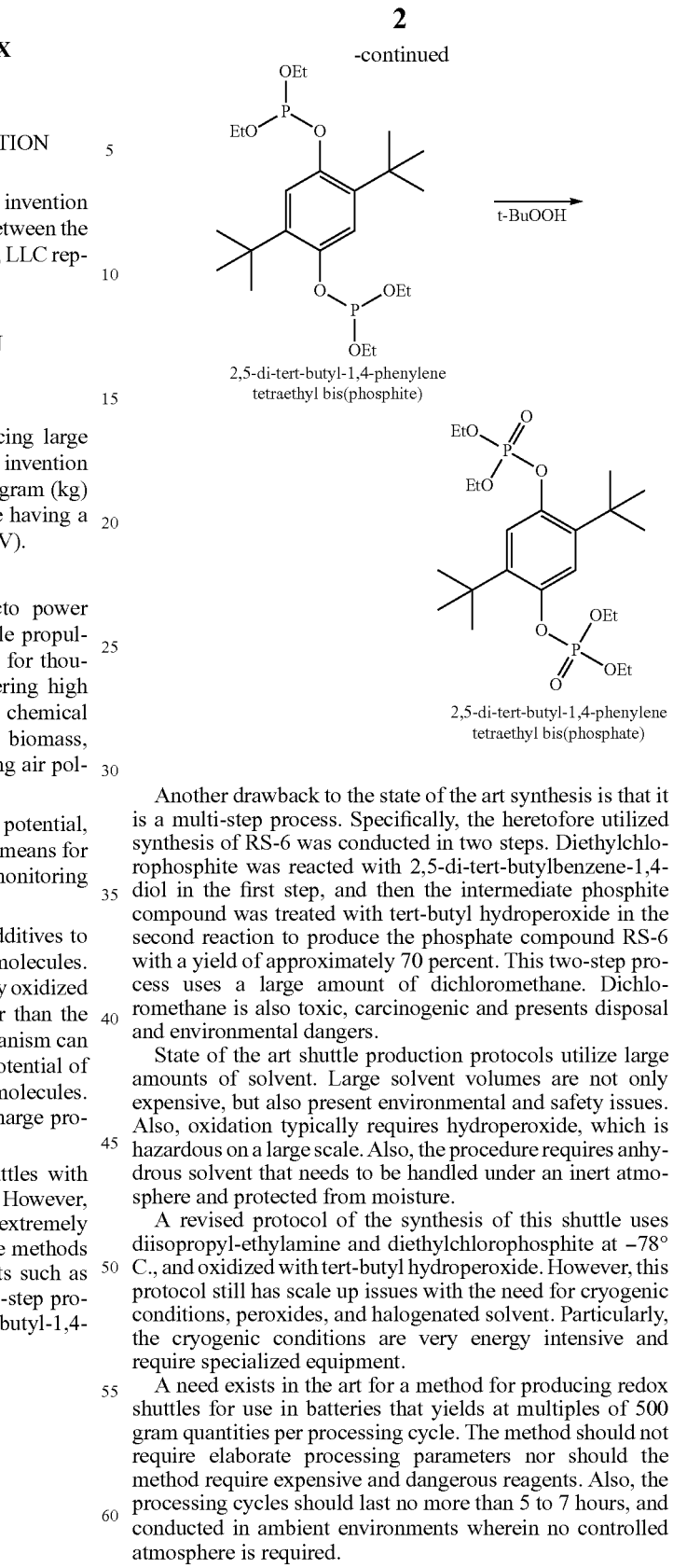

2,5-di-tert-butyl-1,4-phenylene tetraethyl bis(phosphite)

2,5-di-tert-butyl-1,4-phenylene tetraethyl bis(phosphate)

Another drawback to the state of the art synthesis is that it is a multi-step process. Specifically, the heretofore utilized synthesis of RS-6 was conducted in two steps. Diethylchlorophosphite was reacted with 2,5-di-tert-butylbenzene-1,4-diol in the first step, and then the intermediate phosphite compound was treated with tert-butyl hydroperoxide in the second reaction to produce the phosphate compound RS-6 with a yield of approximately 70 percent. This two-step process uses a large amount of dichloromethane. Dichloromethane is also toxic, carcinogenic and presents disposal and environmental dangers.

State of the art shuttle production protocols utilize large amounts of solvent. Large solvent volumes are not only expensive, but also present environmental and safety issues. Also, oxidation typically requires hydroperoxide, which is hazardous on a large scale. Also, the procedure requires anhydrous solvent that needs to be handled under an inert atmosphere and protected from moisture.

A revised protocol of the synthesis of this shuttle uses diisopropyl-ethylamine and diethylchlorophosphite at −78° C., and oxidized with tert-butyl hydroperoxide. However, this protocol still has scale up issues with the need for cryogenic conditions, peroxides, and halogenated solvent. Particularly, the cryogenic conditions are very energy intensive and require specialized equipment.

A need exists in the art for a method for producing redox shuttles for use in batteries that yields at multiples of 500 gram quantities per processing cycle. The method should not require elaborate processing parameters nor should the method require expensive and dangerous reagents. Also, the processing cycles should last no more than 5 to 7 hours, and conducted in ambient environments wherein no controlled atmosphere is required.

SUMMARY OF INVENTION

An object of the invention is to provide a method for production of redox shuttles for lithium ion energy systems that overcomes many of the disadvantages of the prior art.

Another object of the invention is to provide a method for production of redox shuttles that enables batch production of the shuttle in access of 500 grams. A feature of the invention is that substantially all reaction by-product are removed from the final product in a single recrystallization of process. A plurality of crystallization steps can be employed, depending on the purity levels required. An advantage of the invention is that this protocol eliminates the need for chromatography and/or cryogenic conditions, thereby resulting in a process time of between about 5 and 7 hours. Cooling a large reactor to −70° C. can itself take 5-7 hours before even starting the reaction.

Still another object of the present invention is providing a method to produce a redox shuttle that can be conducted in open air. A feature of the method is that no cryogenic conditions, peroxides or halogenated solvents are utilized in the production of the shuttle. An advantage of the invention is that batch quantities of about 400-600 grams (or multiples of about 400-600 grams) are produced between about 2 and 12 hours, preferably between about 5-7 hours, and often within 6 hours.

Yet another object of the present invention is to provide a single step method (wherein a single feedstock compound is modified) for producing a redox shuttle without the need for a controlled atmosphere. A feature of the invention is that the reagents used are stable at ambient temperatures and pressures. An advantage of the invention is its inherent safety.

Briefly, the invention provides for a single step method for producing a redox shuttle having the formula 2,5-di-tert-butyl-1,4-phenylene tetraethyl bis(phosphate), the method comprising phosphorylating tert butyl hydroquinone with a phosphate-containing reagent in a dual phase system.

Also provided is a method for producing 2,5-di-tert-butyl-1,4-phenylene tetraethyl bis(phosphate), the method comprising solubilizing 2,5-di-tert-butylbenzene-1,4-diol and tetrabutylammonium bromide with methyltetrahydrofuran to create a mixture; heating the mixture while adding base to the mixture in an amount to turn the mixture orange; and adding diethyl chlorophosphate to the orange mixture in an amount to phosphorylate the hydroquinone.

BRIEF DESCRIPTION OF DRAWING

The invention together with the above and other objects and advantages will be best understood from the following detailed description of the preferred embodiment of the invention shown in the accompanying drawings, wherein.

DETAILED DESCRIPTION OF THE INVENTION

Figure 1:
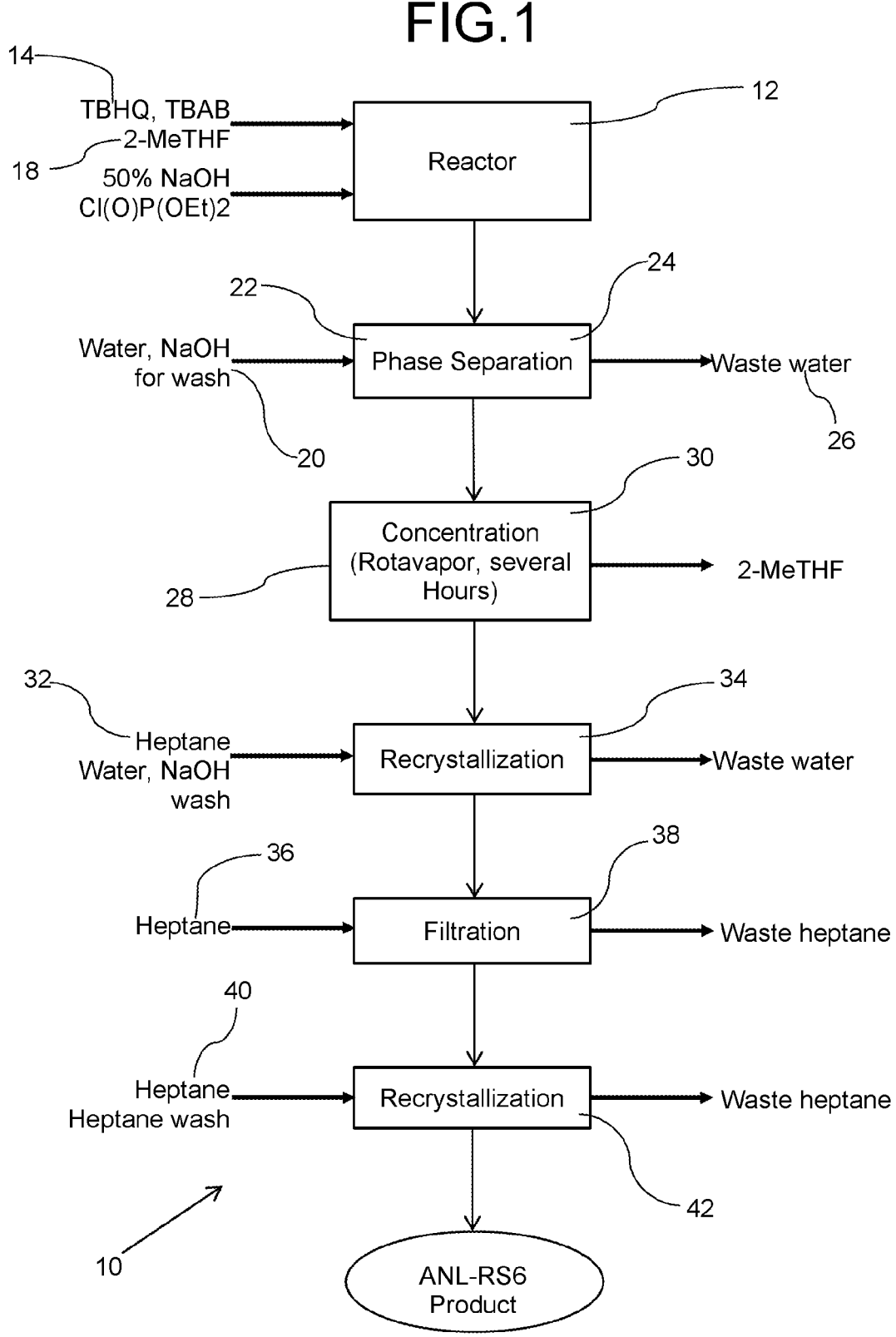
FIG. 1 depicts a flow chart of a process for producing redox shuttle, in accordance with features of the present invention.
Figure 2:
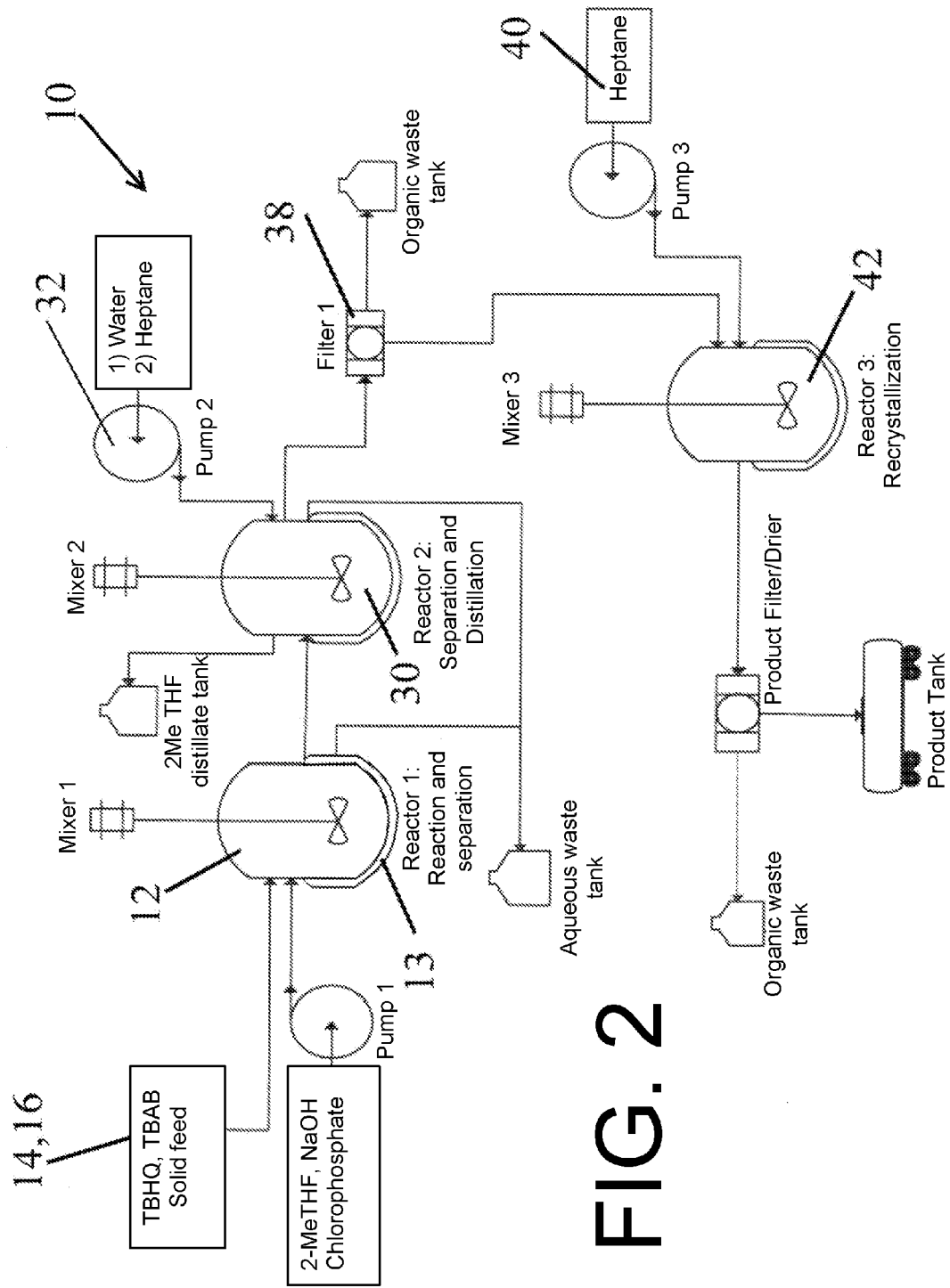
FIG. 2 is a process diagram of a process for producing redox shuttle, in accordance with features of the present invention.

The foregoing summary, as well as the following detailed description of certain embodiments of the present invention, will be better understood when read in conjunction with the appended drawings.

As used herein, an element or step recited in the singular and preceded with the word "a" or "an" should be understood as not excluding plural said elements or steps, unless such exclusion is explicitly stated. Furthermore, references to "one embodiment" of the present invention are not intended to be interpreted as excluding the existence of additional embodiments that also incorporate the recited features. Moreover, unless explicitly stated to the contrary, embodiments "comprising" or "having" an element or a plurality of elements having a particular property may include additional such elements not having that property.

The invention provides a process for producing a high voltage (e.g. more than 4.7 volts) reversible redox shuttle additive in bulk quantities exceeding 500 grams per batch. The additive provides a means for protecting lithium-ion cells from overcharging by relegating the potential of the cathode of the cell to the oxidation potential of the shuttle.

One method for producing this additive is disclosed in L. Zhang et al. *Energy Environ. Sci.,* 2011, 4, 2858-2862, incorporated herein by reference. The overcharge performance of this high voltage shuttle was demonstrated using $LiMn_2O_4$ and $Li_{1.2}Ni_{0.15}Co_{0.1}Mn_{0.55}O_2$ as the cathode materials.

The additive is tetraethyl-2,5-di-tert-butyl-1,4-phenylene bis(phosphate), abbreviated as TEDBPDP, but hereinafter designated herein by its tradename RS-6. A feature of the additive is its incorporation of electron withdrawing groups. These groups, such as organic phosphate moieties, also serve as flame retardants.

Generally, the invented protocol comprises utilization of a dual phase system. An embodiment of the invented protocol comprises an organic phase and an aqueous phase to facilitate a one step process wherein a hydroquinone-based feedstock material (such as 2,5-di-tert-butylbenzene-1,4-diol) is modified by a reagent (such as a chlorophosphate). The dual phase system changes color to indicate various reactions during the protocol. For example, initially, the reaction liquor is substantially colorless. Upon addition of base a first color change (to orange) occurs when a tert-butyl hydroquinone starting material (such as 2,5-di-tert-butylbenzene-1,4-diol) is deprotonated. Then, upon initial completion of the reaction, wherein phosphorylation has occurred, a second color change occurs whereby the liquor changes from orange to yellow. Finally a third color change occurs wherein the liquor changes from yellow to substantially colorless, thereby indicating completion of the process. If the two phases are homogenized, which will occur during mixing, the color changes occur in both phases The feedstock and the reagent are solubilized by a solvent. Suitable solvents are water immiscible solvents, with ethereal solvents preferred. As such, water immiscible solvents selected from the group consisting of methyltetrahydrofuran, tetrahydrofuran, methyl tert-butyl ether, and combinations thereof to create a mixture are suitable. In a preferred embodiment of the invention, a phase transfer catalyst is employed.

In the aqueous phase, a strong base, such as sodium hydroxide dehalogenates phase transfer catalyst in a substitution reaction whereby hydroxyl moiety replaces the halogen anion of the phase transfer catalyst. An excess of the hydroxide assures that substantially all of the PTC exists as the hydroxyl substituted compound. It is this hydroxyl group that facilitates deprotonation of the hydroquinone in the organic phase, discussed infra, with water byproduct. A salient feature of this aqueous step is the generation of relatively innocuous salt (e.g. NaCl, NaBr, etc.) in the aqueous phase.

In the organic phase, the phase transfer catalyst (PTC) is the Bronsted base, extracting a proton or other positively charged moiety from the starting material. Suitable starting material is a hydroquinone with a plurality of alkyl groups. To minimize steric hinderance, and to prevent interaction between moieties, a preferred hydroquinone is where the hydroxyl groups are positioned at opposite sides (i.e., para configuration) of the ring and the alkyl groups are positioned at opposite sides of the ring. Upon deprotonation (which is indicated by a color change to the reaction liquor), a halogenated phosphate moiety is employed as an electrophile to phosphorylate the ring. The halogen of the phosphate moiety serves as the leaving group to rehalogenate the PTC.

Embodiments of the synthesis of the shuttle are depicted in Equations 2-5 below. RS-6 is produced in batches of approximately 2000 grams, without the use of expensive and hazardous reagents. This embodiment represents several improvements to state of the art redox shuttle production schemes. For example, in this embodiment, chlorinated solvents are not utilized, nor are cryogenic conditions Reaction 2 depicts a preferred embodiment of the protocol. Sodium hydroxide and diethyl chlorophosphate are used under phase transfer catalyst conditions in water in the presence of 2-methyltetrahydrofuran. Suitable phase transfer catalysts include, but are not limited to, benzyltriethylammonium, tetrabutylammonium halide, Aliquat (trioctylmethylammonium), benzyltrimethylammonium, tetraoctylammonium, where the counterion includes chloride, bromide, iodide, hydrogen sulfate, or hydroxide, and combinations thereof. This embodiment obviates the need for time consuming chromatographic purification steps. The embodiment also uses heptane as a recrystallization solvent, heptane being a preferred solvent over halogenated solvents utilized in state of the art recrystallization protocols.

Reaction 2:

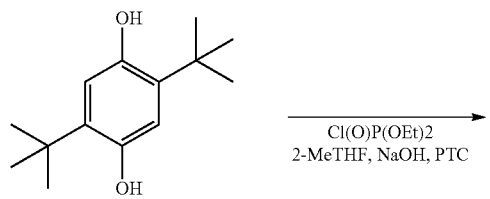

Chemical Formula: $C_{14}H_{22}O_2$
Molecular Weight: 222.32

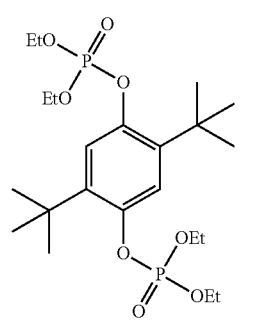

2,5-di-tert-butyl-1,4-phenylene tetraethyl bis(phosphate)
Chemical Formula: $C_{22}H_{40}O_8P_2$ Mol. Wt.: 494.50

Reaction 3 depicts a cost saving improvement to the protocol in Equation 3. Specifically, the $POCl_3$ is a basic industrial chemical and relatively inexpensive compared to diethyl chlorophosphate. Also, the use of phase transfer catalyst is optional. The R in the ROH reagent could be any alkyl group. To arrive at the RS6 shuttle, the alkyl group would be an ethyl, such that the ROH group represents ethanol.

Reaction 3:

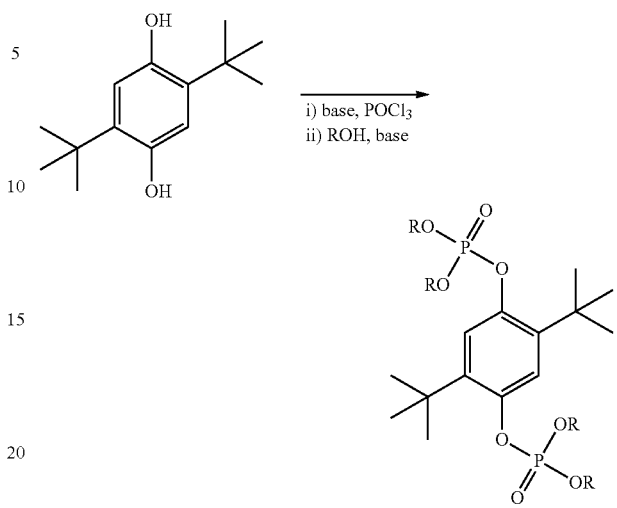

An embodiment of the invented process is a single step reaction protocol. "Single step," as defined in this specification pertains to the conversion of a single feedstock compound, to produce the shuttle. FIG. 1 is a flow chart of this embodiment, the protocol designated therein as numeral 10. First, 2,5-di-tert-butylbenzene-1,4-diol 14 and tetrabutylammonium bromide 16 are placed in a reactor 12. Optionally, an inert atmosphere (e.g., nitrogen or argon, or combinations thereof) is then established within the reactor. Methyltetrahydrofuran 18 is then added to the reactor and mixed with the previously introduced reagents.

Upon mixing of the feedstock, the reagent, the solvent and the catalyst to create a reaction liquor, a temperature-control means 13 of the reactor is set to a temperature of from about 20° C. to 50° C. and preferably about 27° C. Generally, the temperature control means prevent overheating of the liquor, but rather to establish and maintain the liquor at between 20 and 50° C. At this stage, the liquor is colorless in color.

Aqueous solution of sodium hydroxide was added to the reactor in an amount sufficient to deprotonate the phenol on the hydroquinone feedstock compound. Deprotonation is indicated when the initially colorless solution turns color (e.g., orange color).

Phosphate reagent (such as diethyl chlorophosphate, diethyl bromophosphate, diethyl iodophosphate and combinations thereof) was added in amounts sufficient to phosphorylate the dihydroquinone starting material. Surprisingly and unexpectedly, a visual cue is provided for this stage of the process. Specifically, the phosphate moiety is added over time so as to turn the reaction liquor from orange to light yellow in color, then to colorless.

A feature of the temperature control is that the phosphorylation step is maintained at between about 15 to 45° C., preferably at about 23 to 30° C., and most preferably at about 27° C. In an embodiment of the temperature control protocol, the reaction is run while cooling the liquor, given the exothermic nature of the reaction. In an embodiment, heat is added at the start of the chlorophosphate addition at 27. It is not required to apply heat at base-adding step.

A feature of the one step protocol is that the amounts of RS-6 generated will depend proportionately on the amount of hydroquinone parent compound utilized. In an embodiment of the invention, there is approximately a 1:1.5 to 1:2 weight ratio of the hydroquinone amount to the final product amount.

Solvent Extraction Detail

The reaction liquor is cooled and water 20 is stirred into, mixed with or otherwise added to the reaction liquor in amounts sufficient to dissolve salt residing in the aqueous phase, inasmuch as the salt is produced in sufficient quantity to partially precipitate. The water-liquor is then thermally treated 24 and or stirred to facilitate solubilization of any precipitated salts for their subsequent removal. In an embodiment of the invention, the water is maintained at room temperature (e.g. 23 C) or slightly higher to facilitate solubilization of salts. Then, the stirring is stopped so as to allow a phase separation to occur.

The bottom aqueous layer 26 is removed and the remaining organic layer is washed 20 with base such as sodium hydroxide and water.

The washed organic layer is evaporated or otherwise removed 28 from the reaction chamber to leave residue containing the product. The product 30 is then re-solvated in the same reaction chamber with suitable solvent 32 such as heptane, methyl tert-butyl ether, hexane, pentane, trimethylpentane, and combinations thereof. In an embodiment of the invention, heptane is added to the reaction chamber and heated to dissolve the solids. Suitable heating temperatures are from 40° C. to 90° C. and preferably about 60° C.

This organic phase is washed 32 with sodium hydroxide and twice with water after which the solution is cooled while stirred. An exemplary cooling protocol is where the solvent is cooled to about 20 degrees during the course of a working shift (6-8 hours) while stirred at a speed of about 100-130 rpm.

Solid product 34 formed during the aforementioned cooling step is washed 36 in solvent and re-dissolved. It is this first recrystallization step where substantially all of the impurities are removed from the final product, thereby eliminating the need for chromatography. Seed crystals were added to initiate precipitation of product.

After cooling of the suspension, the resulting solids are filtered 38 and washed 40 with solvent then dried at above the final cooling temperature. About an 80-85 percent yield is realized. Yields of final products will depend upon the quantity of feedstock hydroquinone utilized. However, given the invented purification protocol, sans chromatography, purity of the final product 42 is greater than 99 percent.

Generally, the weight percent ranges of the reagents used in an embodiment of the invention include the following.

|  | Weight Percent Range to Total Liquor | |
|---|---|---|
| Reagent | Low | High |
| Foundation Molecule (e.g. tertbutylhydroquinone) | 3 | 9 |
| Base (e.g. sodium hydroxide) | 7 | 10 |
| Solvent (e.g. methyltetrahydrofuran) | 66 | 70 |
| PTC (e.g. tetrabutylammonium bromide) | .1 | .8 |
| Phosphate | 14 | 21 |

Testing Detail

Redox shuttle produced via the invented streamlined protocol was implemented with the following battery constituents:

Electrolyte: 5% RS6 in 1.2M $LiPF_6$ Ethyl Carbonate/Ethyl Methyl Carbonate (EC/EMC) (3/7);
Cathode: $LiMn_2O_4$
Anode: Graphite
2032 Coin cell, Celgard® 2325 separator Example 1

Specific amounts of reactants are determined empirically to affect these changes to the hydroquinone feedstock.

Table 1, infra provides specific amounts for illustrative purposes in the production of about 31 kilograms of the desired shuttle, herein designated by its tradename RS6™.

TABLE 1

Reactant Amounts to produce redox shuttle RS6 ™

|  | Amount (kg) | Capacity (L) | Rate (L/h) | Temp (° C.) | RPM |
|---|---|---|---|---|---|
| Solid Feed 1: TBHQ | 17 | | | | |
| Solid Feed 1: TBAB | 0.77 | | | | |
| Pump 1: 2-MeTHF | 140 | 200 | 200 | | |
| Pump 1: 50% NaOH | 12 | 17 | | | |
| Pump 1: Chlorophosphate | 35 | | | | |
| Pump 1: Water | 17 | | | | |
| Reactor 1 | | 400 | | 10-110 | |
| Mixer 1 | | | | | 0 to 150 |
| Aqueous Waste tank | 29 | 100 | | | |
| Reactor 2 | | 400 | | 10-110 | |
| Mixer2 | | | | | 0 to 150 |
| Pump 2: Water | 34 | | 530 | | |
| Pump 2: Heptane | 156 | 230 | | | |
| Aqueous Waste 1 | 34 | 100 | | | |
| Distillate tank | 140 | 200 | | | |
| Filter 1 | (40) | 100 | | | |
| Organic Waste Tank 1 | 156 | 200 | | | |
| Reactor 3 | | 400 | | 10-110 | |
| Mixer 3 | | | | | 0 to 150 |
| Pump 3: Heptane | 156 | | 400 | | |
| Product Filter/Drier | | 50 | | 10-50 | |
| Organic Waste Tank 2 | 156 | 200 | | | |
| Product RS6 | 31 | | | | |

Example 2

A glass reactor (20 L, jacketed, Chemglass) equipped with drain valve, internal temperature probe, reflux condenser, gas inlet/outlet adapters and powder port was flushed with argon. The jacket of the reactor was connected to a Huber 430 heating/chilling circulator. An argon flow was continued to inert the reactor.

2,5-di-tert-butylbenzene-1,4-diol (1010 g, 4.5 mol, Aldrich MKBG8404V) and tetrabutylammonium bromide (45.2 g, 0.13 mol, Aldrich MKBG5872V) were charged to the reactor. 2-Methyltetrahydrofuran (10 L, MKBG1620V) was added to the reactor and the stirrer was started. The temperature control unit was set to 27° C. and started. A 50% aqueous solution of sodium hydroxide (1470 g, 18 mol, Aldrich MKBG1414) was added, turning the solution an orange color. A peristaltic pump was set up to deliver diethyl chlorophosphate (2038 g, 11.8 mol, TCl lot NFJTB) over a 70 minute period.

By the end of the addition, the reaction had turned color from orange to light yellow to colorless. HPLC analysis indicated the reaction was complete. The reactor contents were cooled to 15° C. and water (2.6 L) was added. The mixture was warmed to 23° C. and the stirring was stopped.

The bottom aqueous layer was removed. The organic layer was washed with 10% NaOH (2 L) and water (2 L). The solvent was then removed on a Buchi rotary evaporator (R-215, bath temperature 40 C, pressure 85-90 mbar).

The 20 L reactor was cleaned and the rotovap residue was transferred back to the 20 L reactor using 4 L of heptane. A total of 12 L of heptane was added and the mixture was heated to 60° C. to dissolve the solids. The solution was washed with 10% aqueous NaOH (2.5 L) and twice with water (2.5 L).

The solution was cooled from about 58° C. to about 21° C. over approximately a 6 hour period at a stirring speed of 115 rpm. The solids were filtered and rinsed with heptane (approximately 1 L). The solids were transferred back to the 20 L reactor and dissolved in about 12 L of hot heptane. The solution was then heated to distill off some remaining water. The dry solution was then cooled to about 54° C., when seed crystals were added. Over several minutes, a significant amount of solids formed. The suspension was kept at about 54° C. for about 1 hour, then cooled to about 21° C. over about 480 minutes. This facilitates ageing the suspension whereby the solution is seeded to obtain an initial crop of crystals. These crystals are held at elevated temperature to equilibrate. This provides a means to facilitate the resolubilizing of impurities trapped in the first crystals. The ultimate yield is a suspension of highly pure crystals. This ageing process further provides a means to maximize the bulk of the recrystallization upon further cooling.

The solids were filtered and washed with heptane (2×1 L), then dried at about 30° C. in a vacuum oven to obtain 1815 g (81% yield). Purity was 99.01% (average HPLC peak area integration). Moisture was 190 ppm (average per KF coulometric titration). Melting point was about 87-89° C. FTIR and NMR agree with the proposed structure.

In summary, the invented protocol provides a method for producing redox shuttle in industrial-sized quantities. Generally, doubling or tripling the amount of starting material hydroquinone, with a concomitant increase in the amount of solvent and other reactants, will cause a doubling in the yield of the shuttle.

It is to be understood that the above description is intended to be illustrative, and not restrictive. For example, the above-described embodiments (and/or aspects thereof) may be used in combination with each other. In addition, many modifications may be made to adapt a particular situation or material to the teachings of the invention without departing from its scope. While the dimensions and types of materials described herein are intended to define the parameters of the invention, they are by no means limiting, but are instead exemplary embodiments. Many other embodiments will be apparent to those of skill in the art upon reviewing the above description. The scope of the invention should, therefore, be determined with reference to the appended claims, along with the full scope of equivalents to which such claims are entitled. In the appended claims, the terms "including" and "in which" are used as the plain-English equivalents of the terms "comprising" and "wherein." Moreover, in the following claims, the terms "first," "second," and "third," are used merely as labels, and are not intended to impose numerical requirements on their objects. Further, the limitations of the following claims are not written in means-plus-function format and are not intended to be interpreted based on 35 U.S.C. §112, sixth paragraph, unless and until such claim limitations expressly use the phrase "means for" followed by a statement of function void of further structure.

As will be understood by one skilled in the art, for any and all purposes, particularly in terms of providing a written description, all ranges disclosed herein also encompass any and all possible subranges and combinations of subranges thereof. Any listed range can be easily recognized as sufficiently describing and enabling the same range being broken down into at least equal halves, thirds, quarters, fifths, tenths, etc. As a non-limiting example, each range discussed herein can be readily broken down into a lower third, middle third and upper third, etc. As will also be understood by one skilled in the art all language such as "up to," "at least," "greater than," "less than," "more than" and the like include the number recited and refer to ranges which can be subsequently broken down into subranges as discussed above. In the same manner, all ratios disclosed herein also include all subratios falling within the broader ratio.

One skilled in the art will also readily recognize that where members are grouped together in a common manner, such as in a Markush group, the present invention encompasses not only the entire group listed as a whole, but each member of the group individually and all possible subgroups of the main group. Accordingly, for all purposes, the present invention encompasses not only the main group, but also the main group absent one or more of the group members. The present invention also envisages the explicit exclusion of one or more of any of the group members in the claimed invention.

The invention claimed is:

1. A single step method for producing a redox shuttle having the formula 2,5-di-tert-butyl-1,4-phenylene tetraethyl bis(phosphate), the method comprising phosphorylating tert butyl hydroquinone with a phosphate-containing reagent in a dual phase system wherein the dual phase system comprises an aqueous solution of base and a water-immiscible organic solvent in the presence of a phase-transfer catalyst, and wherein the method occurs at between about 20 and 35° C.

2. The method as recited in claim 1 wherein the phosphate-containing reagent is a halogenated compound selected from the group consisting of diethyl chlorophosphate, diethyl bromophosphate, diethyl iodophosphate and combinations thereof.

3. The method as recited in claim 1 wherein the shuttle is purified without the use of chromatography.

4. The method as recited in claim 3 wherein the shuttle is produced in about 5 to 7 hours.

5. The method as recited in claim 1 wherein the phosphorylating occurs in ambient atmosphere.

6. The method as recited in claim 1 wherein the hydroquinone and reagent are solubilized with water immiscible solvents selected from the group consisting of methyltetrahydrofuran, tetrahydrofuran, methyl tert-butyl ether, and combinations thereof to create a mixture.

7. A single step method for producing a redox shuttle having the formula 2,5-di-tert-butyl-1,4-phenylene tetraethyl bis(phosphate), the method comprising phosphorylating tert butyl hydroquinone with a phosphate-containing reagent in a dual phase system, wherein the dual phase system comprises an aqueous solution of base and a water-immiscible organic solvent in the presence of a phase-transfer catalyst.

8. The method as recited in claim 1 further comprising a visual cue to indicate the phosphorylation.

9. The method as recited in claim 1 wherein the dual phase system changes color to indicate phosphorylation.

10. A method for producing 2,5-di-tert-butyl-1,4-phenylene tetraethyl bis(phosphate), the method comprising:
   a. solubilizing 2,5-di-tert-butylbenzene-1,4-diol and tetrabutylammonium bromide with methyltetrahydrofuran to create a mixture;
   b. adding base to the mixture in an amount to turn the mixture orange; and
   c. adding diethyl chlorophosphate to the orange mixture in an amount to phosphorylate the hydroquinone.

11. The method as recited in claim 10 wherein the method utilizes a dual phase reaction liquor.

12. The method as recited in claim 11 wherein dual phase reaction liquor comprises an aqueous solution of base and a water-immiscible organic solvent in the presence of a phase-transfer catalyst.

13. The method as recited in claim 11 wherein the method utilizes a phase transfer catalyst.

14. The method as recited in claim 10 wherein the 2,5-di-tert-butyl-1,4-phenylene tetraethyl bis(phosphate) is purified without the use of chromatography.

15. The method as recited in claim 10 wherein the 2,5-di-tert-butyl-1,4-phenylene tetraethyl bis(phosphate) is produced in about 5-7 hours.

16. The method as recited in claim 10 wherein the method is performed in ambient atmosphere.

17. The method as recited in claim 10 wherein phosphorylation is indicated when the color of the mixture turns from orange to colorless.

18. The method as recited in claim 10 wherein the temperature of the method is controlled between about 10 and 50° C., preferably between about 20 and 35° C., most preferably at about 27° C.

* * * * *